Figure 1:
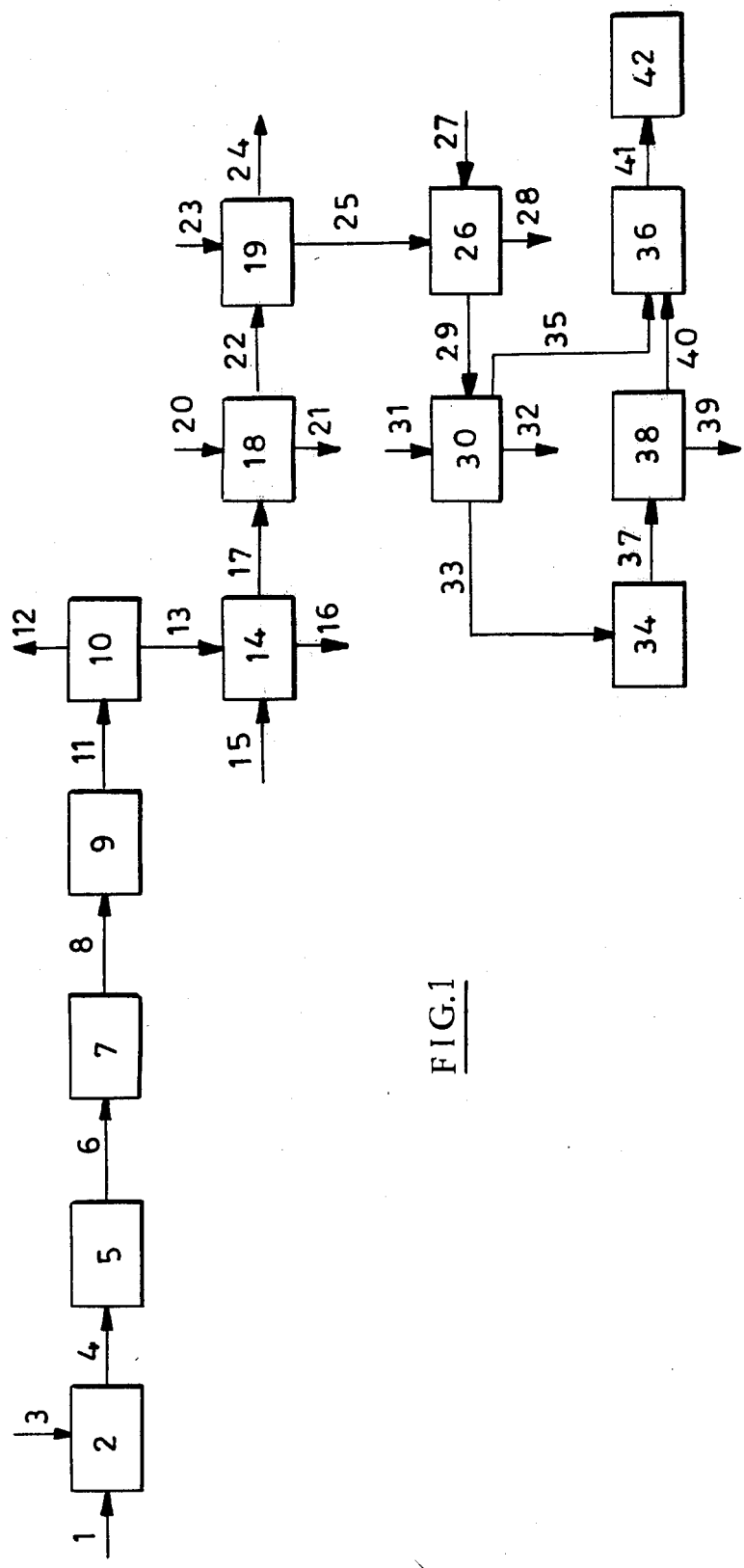

United States Patent [19]

Pende et al.

[11] 4,219,467
[45] Aug. 26, 1980

[54] METHOD FOR THE PREPARATION OF CHORIONIC HUMAN SOMATOMAMMOTROPIN

[75] Inventors: Berislav Pende; Paolo Neri, both of Siena, Italy

[73] Assignee: Istituto Sieroterapico & Vaccinogeno Toscano 'SCLAVO' S.p.A., Siena, Italy

[21] Appl. No.: 965,688

[22] Filed: Dec. 1, 1978

[30] Foreign Application Priority Data

Dec. 27, 1977 [IT] Italy .................................. 31276 A/77

[51] Int. Cl.² ...................... A61K 35/50; C07G 15/00
[52] U.S. Cl. ................................... 260/112 R; 424/95; 424/105
[58] Field of Search .................. 424/95, 99, 100, 105; 260/112 R

[56] References Cited

U.S. PATENT DOCUMENTS 3,201,382  8/1955  Bornstein .......................... 260/112 R
4,123,510  10/1978  Banik et al. ........................ 424/99 X

OTHER PUBLICATIONS

Protides of the Biological Fluids, 24th Colloquium, 1975, published 1976, 24, pp. 61–66, Neri.
Ann. Sclavo, 12, pp. 663–675 (1970), Neri et al.
Nature, 208, pp. 1214–1215 (1965), Friesen.
Biochimica et Biophysica Acta, 322 (1973), pp. 88–94, Neri et al.
Chem. Abstracts, vol. 87, 1977, 194250w, Neri.

Primary Examiner—Howard E. Schain
Attorney, Agent, or Firm—Morgan, Finnegan, Pine, Foley & Lee

[57] ABSTRACT

A method is disclosed for extracting human chorionic somatomammotropin (HCS) which comprises the steps of separating from placental extract a proteinic fraction which contains such hormone, enriching the fraction so as to increase its HCS percentage contents, ultrafiltering and chromatographically analyzing until the liquor volume is gradually reduced and the components of the extract other than the expected hormone are removed.

4 Claims, 1 Drawing Figure

METHOD FOR THE PREPARATION OF CHORIONIC HUMAN SOMATOMAMMOTROPIN

This invention relates to a method for the preparation of human chorionic somatomammotropin (to be defined hereinafter always with the symbol HCS) starting from placental extracts or from proteinic fractions obtained therefrom.

HCS is a hormonal protein contained in the human placenta, which can be used in the therapeutics in cases in which abortion is feared or for resolving other pathological situations in pregnancy.

It has been reliably ascertained that HCS is synthesized exclusively by the placenta: it exhibits a number of biological activities and it is surmised that it has a bearing on the regulation of the anabolism during pregnancy.

The methods known heretofore for the extraction of HCS do not permit the preparation of amounts of it having a sufficient purity and capable of permitting the chemical studies on a large scale to be performed so as to achieve practical applications of such a hormone. Such methods are mainly based on a preliminary extraction with saline solutions, followed by precipitation with cold ethanol. The precipitate is the redissolved and fractionally split with ion-exchangers and gel-filtration. Among others, the Friesen method can be mentioned (Friesen, H.G., Nature, 208 (1965) page 1214) which, by following the procedure summarized above, permits to obtain a yield of 7% relative to the quantity of HCS contained in the starting materials (the initial concentration of HCS is in the order of magnitude of 0.01% to 0.05% by wt relative to the weight of the ejected placenta).

We have now found it possible to obtain HCS up to a yield of 50% and over, at a purity of more than 90%, by separating, from a placental extract or a proteinic fraction derived therefrom, a phase containing HCS and subjecting such a phase to subsequent alternate enrichment treatments, ultrafiltration and chromatography. The adoption of the ultrafiltration procedure, inter alia, permits to prevent repeated precipitations and to reduce the volumes to be treated. The elimination (or, at least, the extreme reduction) of precipitation steps acts in such a way that the biologically active molecules of HCS are constantly maintained in aqueous solutions without any hazard of denaturation or modification of the biological properties. Precipitation may be effected by the use of a precipitating agent selected from ammonium sulfate, sodium sulfate or polyethylene glycol. Conversely, this hazard is continually incurred when performing the conventional methods.

The method according to the present invention can be applied to a number of different raw materials, among which there can be mentioned the placental extract, the raw immunological fraction or the fractions which are eliminated during the purification of immunoglobulins.

As outlined above, the method according to this invention comprises the steps of a preliminary separation, from the placental extract or from a proteinic fraction deriving therefrom, of a phase which is rich with HCS and of a subsequent of alternate treatments of enrichment, ultrafiltration and chromatography.

The enrichment is preferably carried out by ionic exchange. An appropriate selection of the ion-exchangers permits a very accurate selection of the components of the polypeptide fraction having a similar surface electrostatic charge. A careful check of the chromatography procedure (gel-chromatography) permits to isolate an extremely pure fraction with restricted variations of the mol wt of the polypeptides. Ultrafiltration, lastly, is carried out through membranes having a pass-threshold for molecules having a mol wt of 10,000.

The sequential order, the number and the alternation of the several steps, as well as the selection of the most appropriate means for achieving the expected results, are, at any rate, within the purview of anyone skilled in the art, so that, once the principle of the invention has been understood, a skilled technician may introduce optional modifications without, however, departing from the invention in order to arrive at certain results.

Thus, in order that the method may be more clearly illustrated, there will be described, in the following, a particular sequence of the several steps mentioned above. For this reason, reference will also be had to the block diagram depicted in the accompanying drawing, it being understood that the disclosure is merely an example to which routinely modifications can be applied within the scope of this invention.

The starting material (a placental extract or a proteinic fraction) is dissolved in a 0.1 M buffer having a pH of 8 to 9, to give a solution in which HCS is less than 1% of the proteins. Subsequently, the insoluble particles are removed by centrifugation (De Laval separator) and the opalescent aggregates of colloidal nature are removed with a ball centrifuge. The clear supernatant liquid, which is virtually colorless, can be easily removed merely by filtering it off. The filtrate is ultra-filtered and the clarified and concentrated solution is contacted by a ion-exchanger so as to remove the impurities having a similar mol wt but a different electric change.

Another ultrafiltration step is carried out, whereafter an ionic exchange is effected and then ultrafiltration again.

At this stage, chromatographies are started: one fraction contains high-purity HCS and is freeze-dried. A first fraction is, instead, discarded, whereas a second fraction (containing impure HCS) is ultra-filtered and chromatographed once again. The sequence of steps is repeated and, as a total, after freeze-drying, there is obtained HCS having a purity higher than 90% in an amount which exceeds the starting quantity by 50%.

More detailedly, with reference to the single FIGURE of the drawing, the starting material (100 kg) is fed through 1 to 2 where, via 3, it is supplemented by a buffer solution (0.1M, pH 8.3). The turbid solution (HCS is less than 1% of the proteins) is sent, via 4, to 5, wherein it is clarified by means of a De Laval separator at a rate of 250 liters an hour. There are obtained about 450 liters of an opalescent solution which cannot be filtered. The latter, at 7, is further clarified in order to remove the colloidal opalescent aggregates by using a ball centrifuge of the Sharples type. The clear supernatant liquor, which is almost colorless, is filtered and sent, via 8, to 9 wherein it is further clarified by a filtration step through a filter-press (20 by 20 cm) using Seitz K/7 filters. There have been used 100 filters for filtering 420 liters. Through 11, the filtrate is sent to 10 wherein it undergoes a ultrafiltration on a DDS module having a surface of 1.7 sq. m and at 15 atm and a temperature of 7° C.–10° C. There are obtained 35 liters an hour of an ultrafiltrate which is discharged via 12, the final volume being 80 liters. The solution, after having been clarified and concentrated is sent, via 13, to 14 wherein it is contacted by the ion-exchanger DEAE-cellulose (Whatman DE-23) so as to remove the impurities having a similar mol wt but a different electric charge. Elution is effected with a 0.5 M, pH 8.3 buffer (fed via 15). The 0.1 M eluate and washings are discarded (at 16) whereas the 0.5 M fraction of 80 liters is reduced as to its volume. Ultrafiltration (at 18) is carried out on UF Millipore cassettes using a membrane with an exclusion limit of 10,000 daltons so as to repeat the contact with the ion-exchanger on a column of 10 by 100 cm at 17. The final retentate is 4 liters.

The line 20 refers to a feed of a buffer (pH 8.3, 0.1 M). The line 21 is the discharge of the ultrafiltrate. The ion-exchange 19 where the filtrate arrives via 22, is made on DEAE-Sephadex A-25 in order to repeat purification and concurrently to introduce a molecular filtration effect. Through 23 the usual buffer 0.5 M, pH 8.3 is introduced and then via 24, the eluate to be discarded (0.1 M) is eliminated. On account of the reduced volume, it has bee possible to collect a 0.5 M fraction in a solution of 16 liters. Such a fraction, along line 25, is sent to an additional ultrafiltration stage at 26 on UF Millipore cassettes (27 is the feed of the 0.1 M, pH 8.3 buffer and 28 is the line for discharging the reject ultrafiltrate). The final volume is now reduced to 1 liter.

So reduced a volume permits to apply the entire sample of the chromatographic column (at 30, via 29: reference 31 is again the feed of a 0.2-0.5 M buffer, pH 8-9). HCS is measured by radial immunodiffusion and the chromatographic profile is cut into three fractions. Through 32 the first fraction, which does not contain any HCS is discarded. The second fraction is HCS with a 50% purity and is recycled via 33 to ultrafiltration 34. The third fraction is HCS having the purity over 90% and, via 35, it is sent to freeze-drying, at 36.

The fraction which is recycled upon ultrafiltration is chromatographed (at 38, whereat it arrives via 37), into two main fractions. The first fraction, which contains impurities having a high mol wt., is discarded (at 39) and the second fraction, which contains HCS having a purity higher than 90%, is sent, via 40, to freeze-drying (at 36) where it is combined with the third fraction exiting the first chromatography, and the two fractions are freeze-dried together. It is advisable to ultrafilter the combined fractions in order to reduce the volume prior to freeze-drying.

The HCS, as obtained upon freeze-drying (at 41) in the form of a cream-colored powder, is dried at 42 and has a degree of purity over 90%.

EXAMPLE 100 kg of a B1+1 fraction of the Merieux process deriving from subsequent dissolution with ethanol and reprecipitation starting from the placental extract and intended to remove therefrom the albumins and the predominant fraction of the haemoglobulins, lipoproteins and immunoglobulins with a proteinic contents of about 30% have been dissolved during 3 hrs in 700 liters of a 0.1 M solution of $NH_4HCO_3$, pH 8.2. The solution has been clarified to remove the insoluble particles by means of a De Laval separator. Since the solution was still opalescent, centrifuging at 16,000 g has been carried out with a ball centrifuge at a temperature not exceeding 4° C. The resultant solution has been ultrafiltered through a membrane having a limit of exclusion of 10,000 daltons until reaching an appropriate proteinic concentration (4%).

About 40 g/liter of wetted DEAE-cellulose which have been previously activated, have then been added to the HCS solution. The mixture has been stirred for one hour and about 200 liters of a 0.1 M eluate have been discharged. 80 liters of a 0.5 M, pH 8.2 buffer have been added to the ion-exchange resin and the whole has been stirred for two hours. Thus a 0.5 M eluate has been collected the volume of which has been reduced to 20 liters, washed with a 0.1 M buffer and the procedure has been repeated with 20 liters added to an exchanger of the type DEAE-Sephadex A-25. 80 liters of a 0.5 M eluate have been ultrafiltered again to a volume of 2 liters and chromatographed with Sephadex G-75. The first fraction has been discarded and 16 liters of the HCS solution, recovered, has been ultrafiltered to 150 mls and treated again gel-chromatographically. 8 liters of a solution of purified HCS have now been ultrafiltered to a volume of 500 mls and then freeze-dried. The yield of HCS was 50% and the purity was 92%.

We claim:

1. A method for the preparation of human chorionic somatomammotropin (HCS) having a high degree of purity, from placental extracts comprising the steps of separating, from the extract of a proteinic fraction deriving therefrom, by centrifugation a phase which contains HCS and subjecting said phase to treatments of enrichment by ion exchange, ultrafiltration and chromatography.

2. Method according to claim 1, for preparing HCS wherein the initial stage of separation of the proteinic phase is carried out by treating the extract or the fraction obtained therefrom with a precipitating agent.

3. Method for the preparation of HCS according to claim 2, wherein the precipitating agent is selected among ammonium sulfate, sodium sulfate or polyethylene glycol.

4. Method for the preparation of HCS according to claims 1, 2 or 3 wherein ultrafiltration is effected through membranes having a pass-threshold for molecules with a mol wt of 10,000.

* * * * *